United States Patent [19]

Leutwyler et al.

[11] Patent Number: 5,768,737
[45] Date of Patent: Jun. 23, 1998

[54] MECHANICAL-TYPE TOOTHBRUSH HAVING A REMOVABLE BRUSHHEAD

[75] Inventors: Robert Leutwyler, Boppelsen; Werner Leutwyler, Zurich, both of Switzerland

[73] Assignee: Johnson & Johnson Consumer Products, Inc., Skillman, N.J.

[21] Appl. No.: 871,311

[22] Filed: Jun. 9, 1997

Related U.S. Application Data

[63] Continuation of Ser. No. 667,761, Jun. 21, 1996, abandoned, which is a continuation of Ser. No. 359,665, Dec. 20, 1994, abandoned.

[30] Foreign Application Priority Data

Dec. 30, 1993 [DE] Germany .......................... 43 45 003.2

[51] Int. Cl.$^6$ ...................................................... A46B 9/04
[52] U.S. Cl. .......................... 15/167.1; 15/145; 15/176.6; 15/176.1; 403/320
[58] Field of Search .................................. 15/167.1, 145, 15/167.2, 176.1, 176.2, 176.3, 176.4, 176.5, 176.6, 172, 184, 185; 403/315, 320

[56] References Cited

U.S. PATENT DOCUMENTS

| | | | |
|---|---|---|---|
| 1,702,042 | 2/1929 | Doskow | 15/176.6 |
| 1,705,542 | 3/1929 | Ryser | 15/176.2 |
| 2,689,967 | 9/1954 | Mackey | 15/176.2 |
| 2,749,567 | 6/1956 | Krueger | 15/172 |
| 2,789,304 | 4/1957 | Leavin | 15/184 |
| 2,913,750 | 11/1959 | Aversa | 15/184 |
| 4,106,152 | 8/1978 | Hadary | 15/176.4 |
| 4,370,773 | 2/1983 | Hadary | 15/176.4 |

FOREIGN PATENT DOCUMENTS

| | | | |
|---|---|---|---|
| 649074 | 8/1928 | France | 15/172 |
| 702369 | 1/1931 | France | 15/172 |
| 178122 | 11/1906 | Germany | 15/176.5 |
| 2402521 | 7/1975 | Germany | 15/176.1 |
| 1996 | of 1905 | United Kingdom | 15/176.1 |

*Primary Examiner*—Gary K. Graham

[57] ABSTRACT

A toothbrush includes a brush part and a hollow handle part exhibiting an axial bearing, a coupling rod, which is slidably mounted in the axial bearing and which is connected to the brush part, a return spring, which is pretensioned on the coupling rod in the direction of the handle part opposite the brush part, and a latching device for rotationally locking the coupling end of the brush part and the coupling end of the handle part. A securing device serves to prevent axial motion of the coupling rod. A first part of the securing device is associated with the coupling rod and a second part of the securing device is associated with the handle part. The second part of the securing device is movable between a securement setting and a release setting and is pretensioned by a spring in the direction of the securement setting. An actuating device in the wall of the handle part serves to actuate the second part of the securing device. An axial motion of the brush part relative to the handle part, for releasing the rotationally secure connection of the two parts, is therefore reliably prevented.

14 Claims, 8 Drawing Sheets

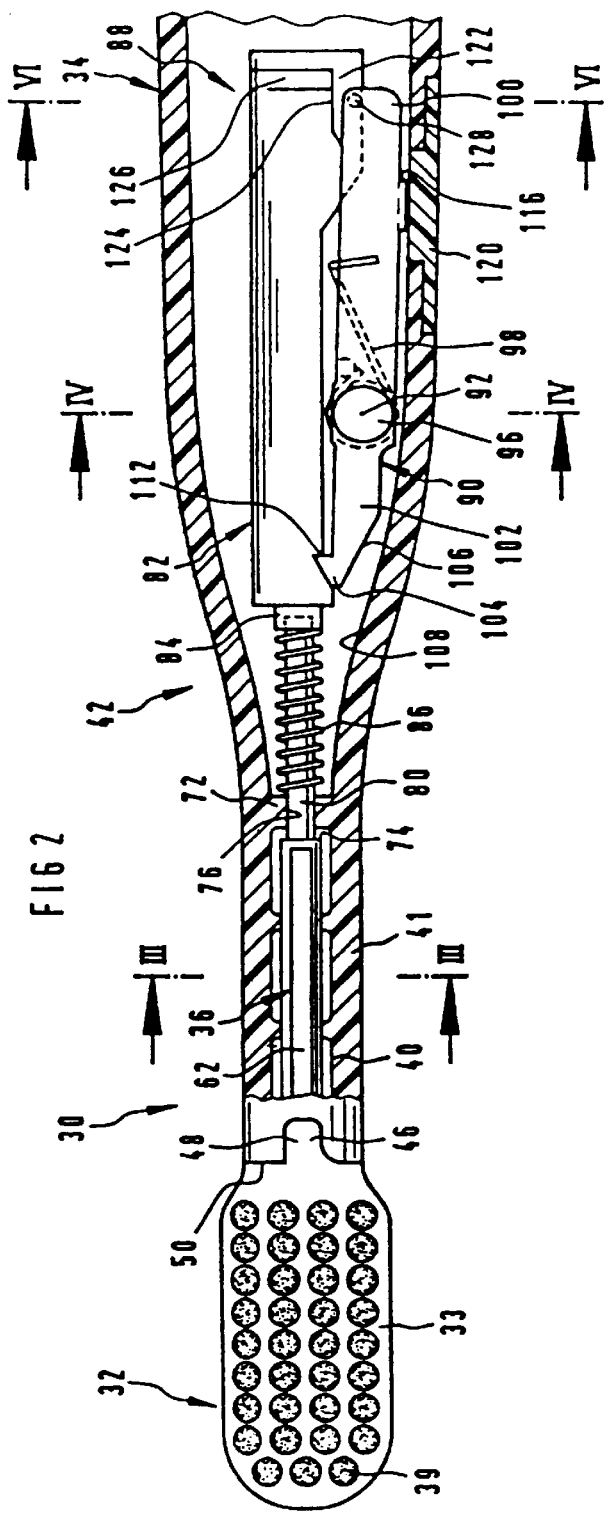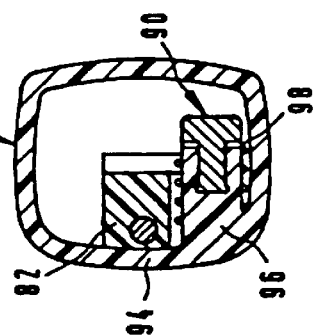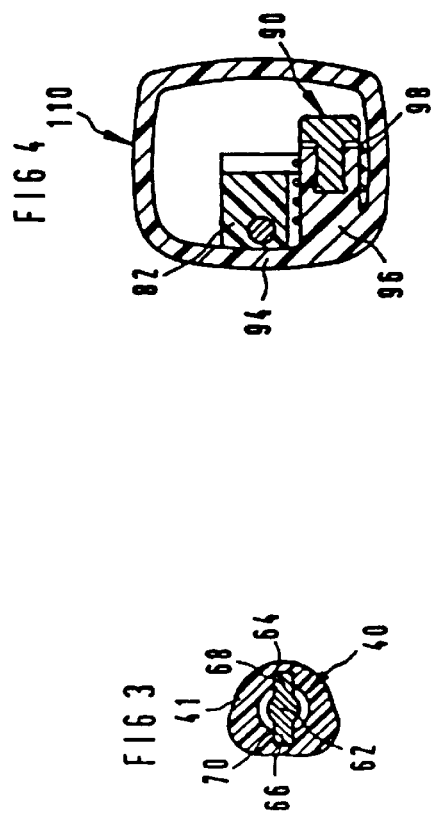

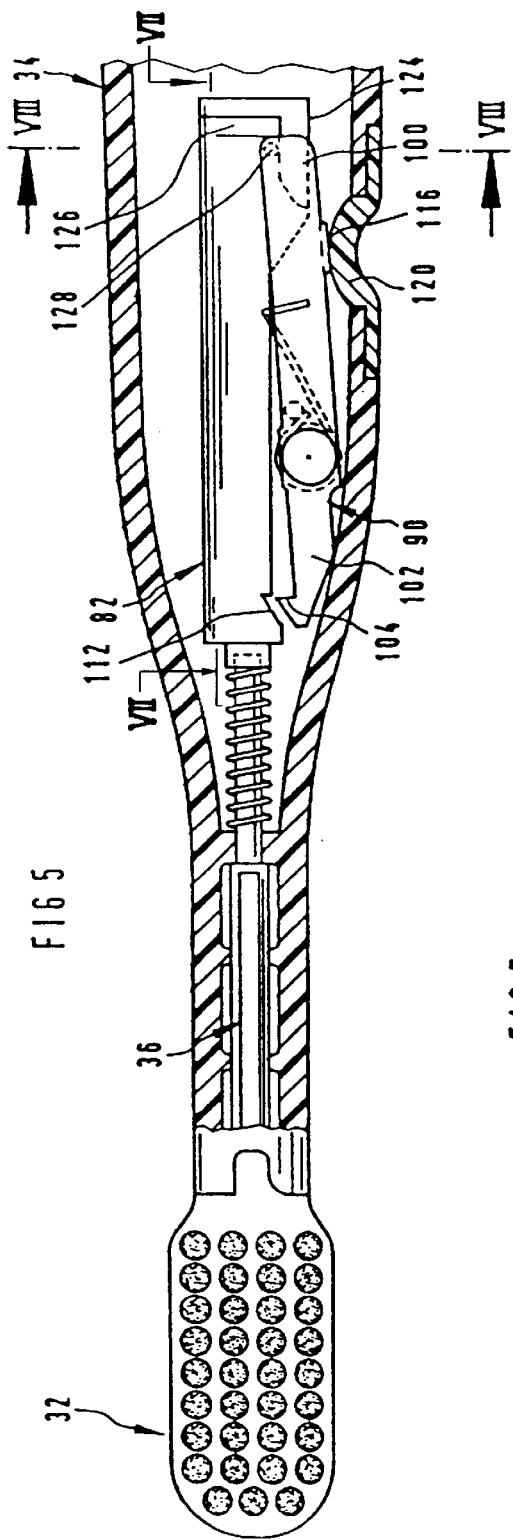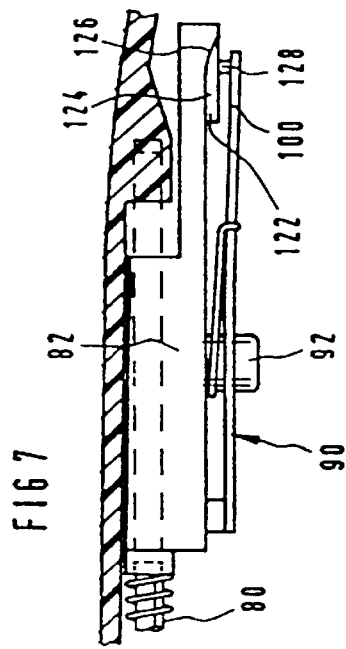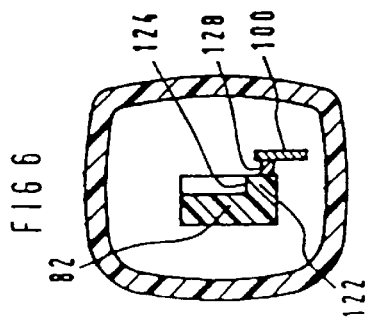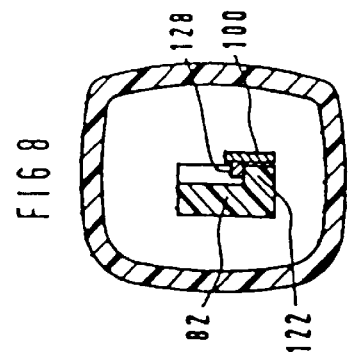

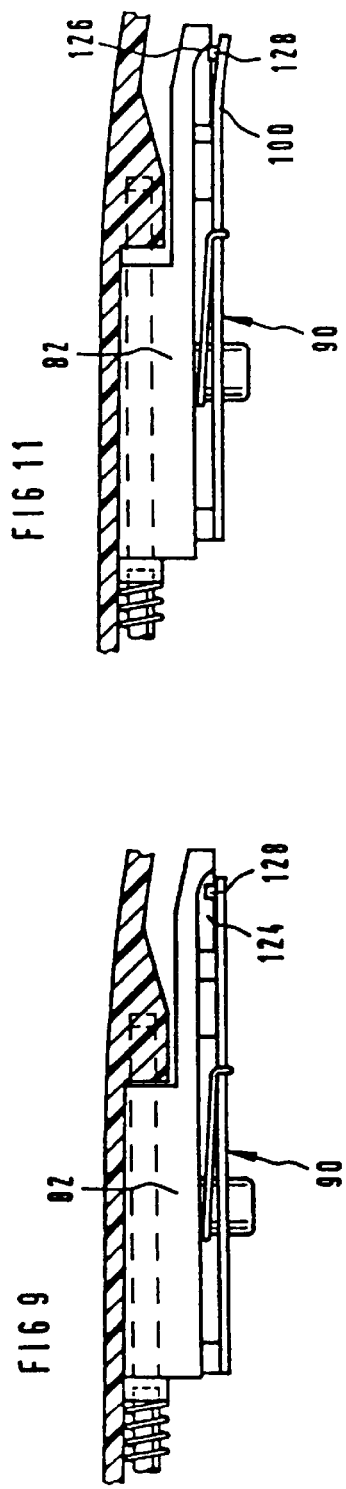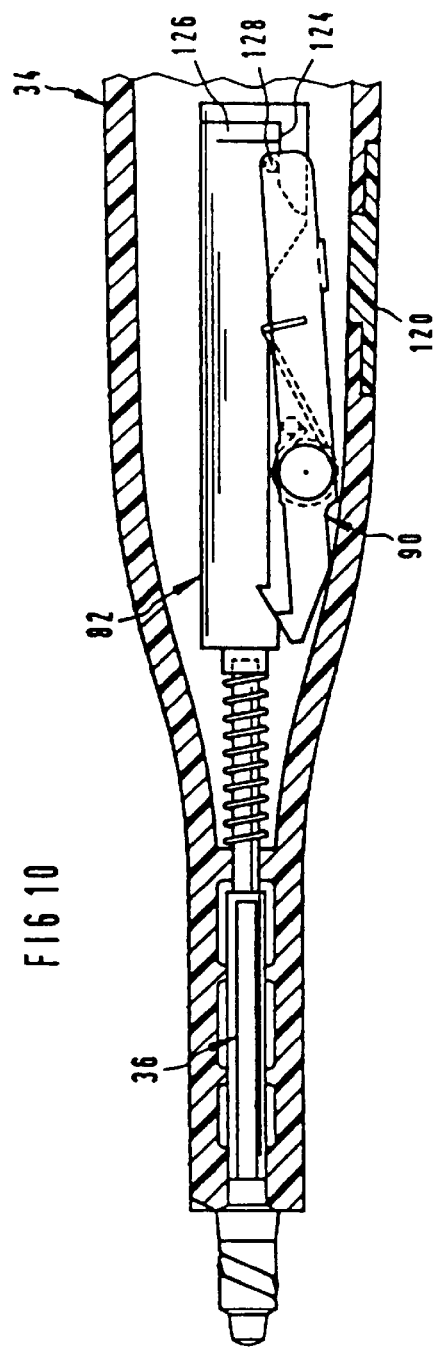

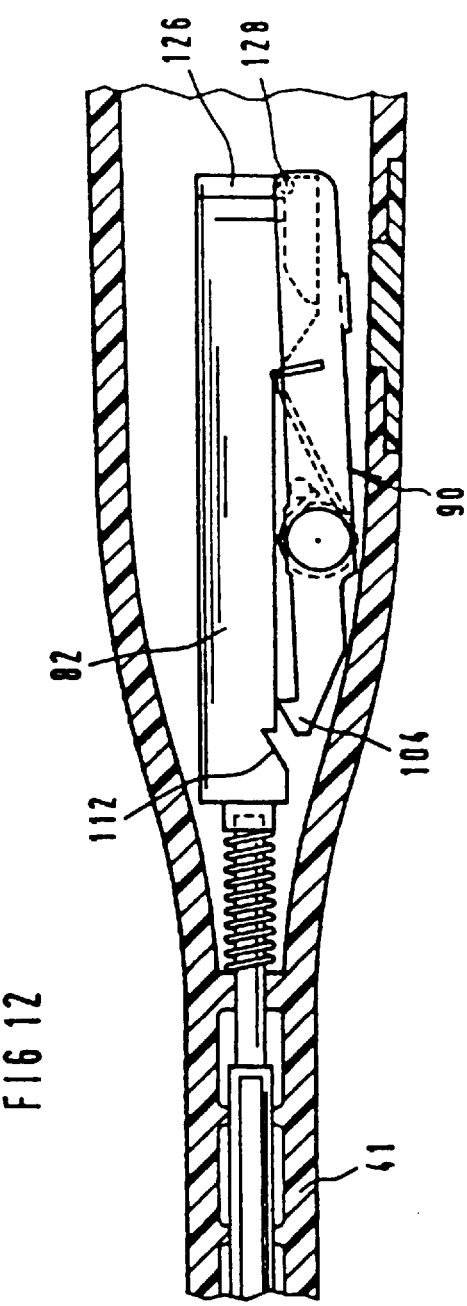

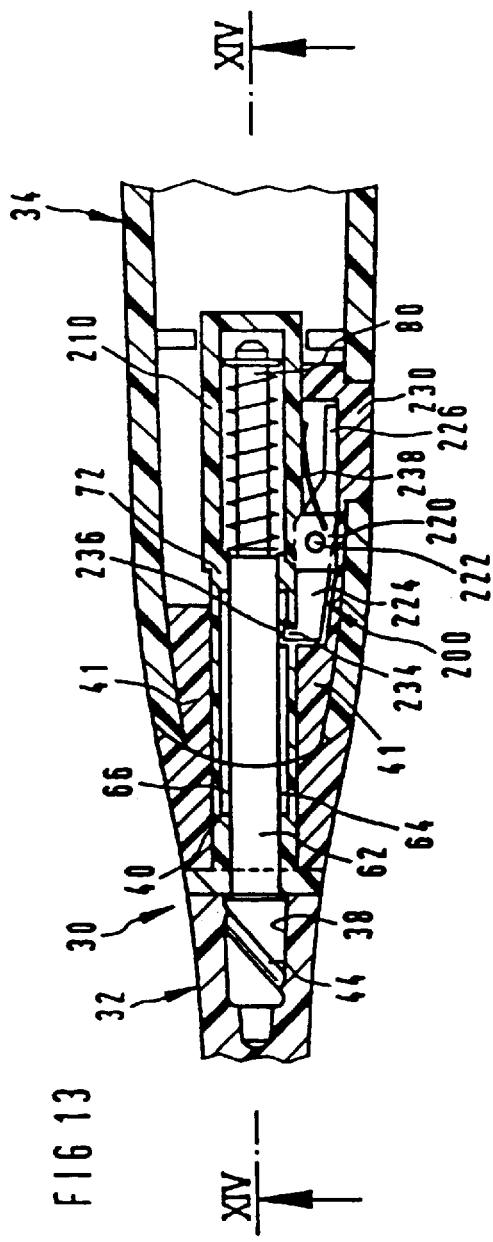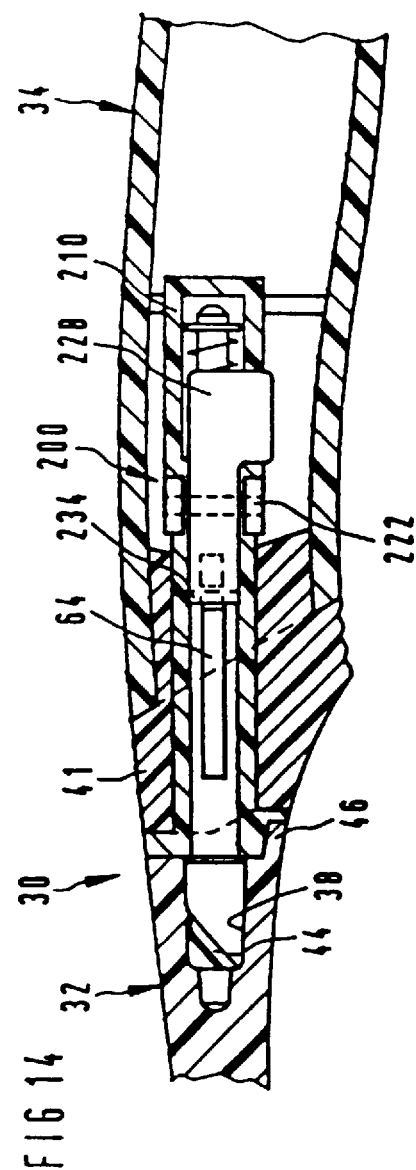

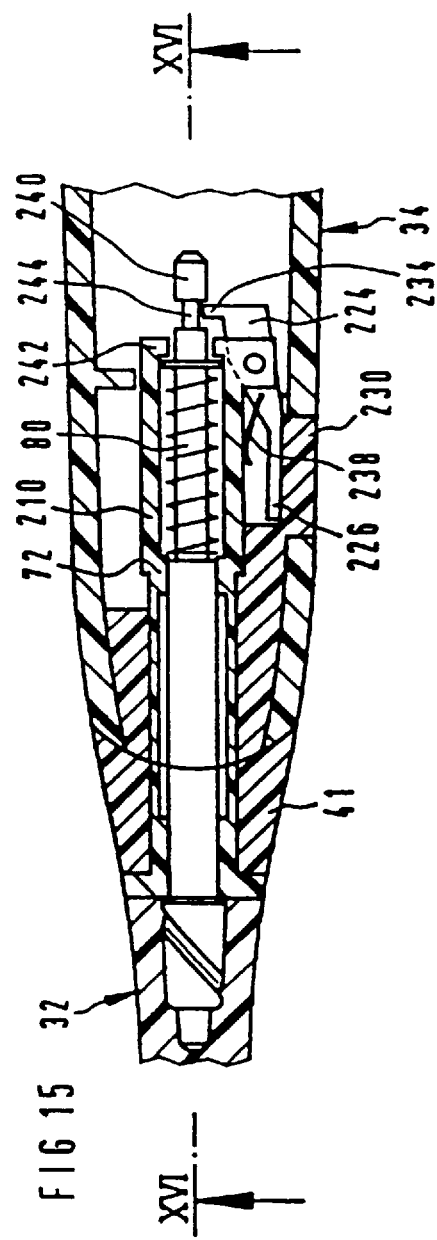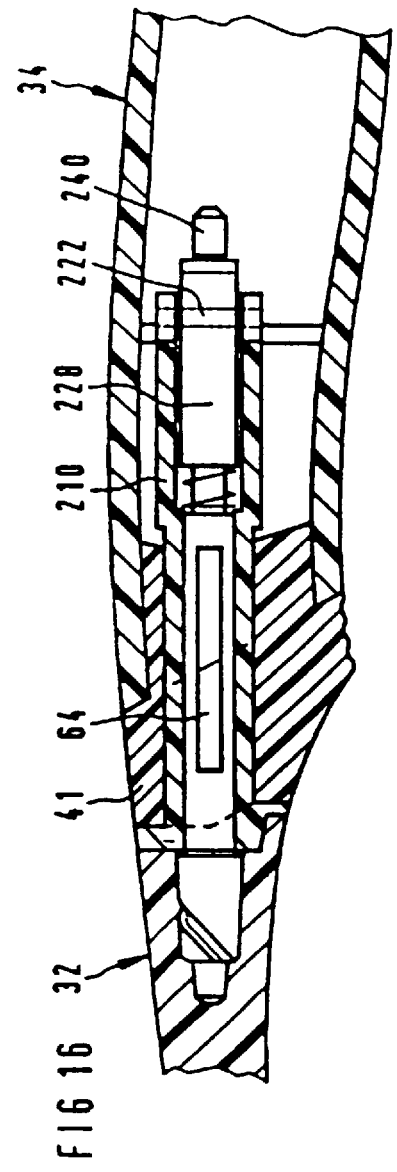

5,768,737

MECHANICAL-TYPE TOOTHBRUSH HAVING A REMOVABLE BRUSHHEAD

This is a continuation of application Ser. No. 08/667,761, filed Jun. 21, 1996, now abandoned, which is a continuation of application Ser. No. 08/359,665, filed Dec. 20, 1994, now abandoned, both of which are hereby incorporated by reference.

BACKGROUND OF THE INVENTION

The invention relates to a toothbrush having the desired characteristic of a removable and therefore, replaceable brushhead.

When a used brush such as the type disclosed in DE 4136537 C1 is removed from the handle part of this known toothbrush, the brush part has to be pulled quite a long way out of the handle before it can be detached, by a rotational motion, from the screw thread of a threaded pin located at the protruding end of the coupling rod. For this purpose, the coupling rod must firstly be moved in the handle part a certain distance axially away, counter to the action of the return spring.

SUMMARY OF THE INVENTION

The object of the invention is to improve the abovementioned known toothbrush such that the described axial relative motion of the brush part relative to the handle part, for releasing the rotationally secure connection of the two parts, can be reliably prevented.

The effect of using a securing device to accomplish this object is that under no circumstances can the brush part be moved into a dismantling setting by a relative axial motion relative to the handle part, when this is not intended. Accordingly, the actuating device has to be actuated in order for a used brush part to be removed and for a new brush part to be fitted to the handle part. Moreover, the design of the actuating device and of the pretensioning spring acting on the coupling rod enables an additional facility for preventing the detachment of the brush part from the handle part by smaller children.

According to a preferred embodiment of the invention, the coupling rod is simultaneously configured as a control device, which interacts with a locking lever. This control device for the locking lever is designed such that when the brush part is fitted, as a result of the locking lever being unlocked by the actuating device, the locking lever is moved into the range of influence of a control cam and is held by the control cam in the unlocked setting, counter to the force of a pretensioning spring, up to an axial setting of the coupling rod in which the brush part can be unlatched and detached from the handle part. In this setting, the locking lever slides out of the control cam, so that the locking lever is moved, under the action of the pretensioning spring acting on it, into a pre-locking setting in which the locking catch slides along a control rod, configured in one part with the coupling rod, to the point where the locking paw of the locking lever falls into a locking groove of the control rod under the influence of the pretensioning force of the spring acting on the locking lever and thereby locks the coupling rod and the brush part connected thereto such that they are axially immovable.

BRIEF DESCRIPTION OF THE DRAWINGS

The invention is described more closely below, in greater detail, with reference to the schematic drawing of a plurality of illustrative embodiments of a toothbrush according to the invention, in which drawing:

FIG. 2 shows a projection of the front side of the toothbrush in partially fragmented and horizontally cut representation for illustrating the coupling device in the locked assembly setting of a brush part on the handle part of the toothbrush;

FIG. 3 shows a cross-section along the line III—III in FIG. 2 through the neck of the toothbrush;

FIG. 4 shows a section along the line IV—IV in FIG. 2 through the coupling rod and the swivel axle of a locking lever of the coupling device;

FIG. 5 shows the toothbrush in a representation similar to FIG. 2, in which, however, the unlocked locking lever is held in the unlocked setting by a control cam of the coupling device;

FIG. 6 shows a cross-section along the line VI—VI in FIG. 2, showing a control cam and a feeler arm of the control device in the handle part of the toothbrush;

FIG. 7 shows a side sectional view of the coupling device along the line VII—VII in FIG. 5;

FIG. 8 shows a cross-section along the line VIII—VIII in FIG. 5, in which the feeler arm of the locking lever bears against the control cam of the coupling device;

FIG. 9 shows a side sectional view of the coupling device along the line VII—VII in FIG. 5, exhibiting the feeler arm of the locking lever, which feeler arm bears against the control cam,;

FIG. 10 shows an essentially horizontal section through the toothbrush similar to FIGS. 2 and 5, only the handle part however, following the removed brush part, being shown in the original setting of the coupling rod of the toothbrush;

FIG. 11 shows a side sectional view of the coupling device along the line VII—VII FIG. 5;

FIG. 12 shows a horizontal section of the handle part in fragmented representation and exhibiting the coupling device in top view, the coupling device being shown in an assembly setting of the coupling rod as a brush part is fitted onto the front coupling end of the coupling rod;

FIG. 13 shows a second embodiment of a toothbrush exhibiting a simple child-prevention securement, in an essentially horizontal section;

FIG. 14 shows a vertical section along the line XIV—XIV in FIG. 13;

FIG. 15 shows a horizontal section through a further embodiment of a toothbrush in partially fragmented representation;

FIG. 16 shows a side view of the toothbrush in FIG. 15 according to the sectional line XVI—XVI;

DETAILED DESCRIPTION OF THE PREFERRED EMBODIMENTS

Figure 1:
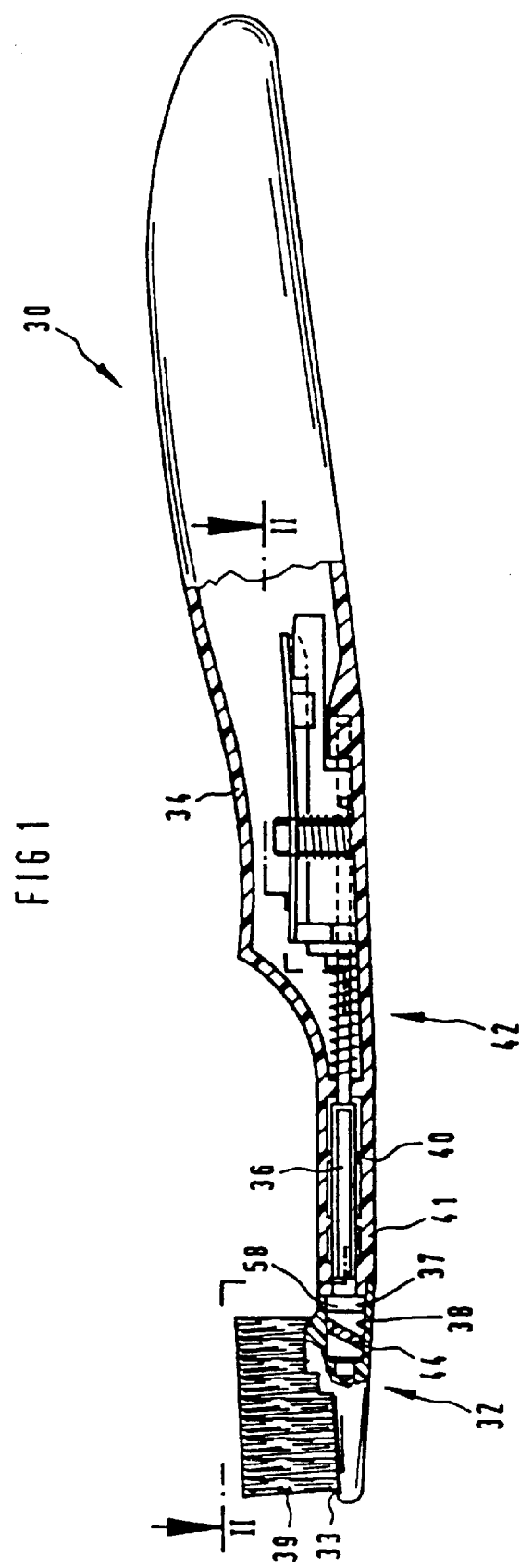
FIG. 1 shows a side view of a first embodiment of a toothbrush according to the invention in partially fragmented representation of a coupling device connecting a brush part to a handle part of the toothbrush.

FIGS. 1 and 2 illustrate a toothbrush 30, the brush part 32 of which is removably fastened to a handle part 34. A coupling rod 36, which is preferably made of plastic and projects from the front end of the handle part 34 facing the brush part 32, can be screwed into an integral coupling opening 38, provided with a screw thread, in the brush part, which brush part is disposed in a reinforced part of a bristle bed 33, the reinforced part receiving bristles 39 of the brush part 32, in a rear end of the brush part 32 facing the handle part 34.

The coupling rod 36 is mounted in an axial sliding bearing 40 in the front end of a neck 41 of the handle part 34, such that it can be moved to a limited extent axially, counter to the force of a pretensioning device 42, out of the front end of the handle part 34, yet cannot be rotated. The coupling rod 36 is provided at its front end with a thread 44, which can be screwed into the coupling opening 38 in the brush part 32. The thread has an angle of rotation of no more than 180°. Projecting axially from the rear end of the brush part 32, on the side of the bristles 39, is a stop cam 46, which is matched by an axial recess 48 in the front end of the handle part 34. As the brush part 32 is screwed on, the stop cam 46, after a small angle of rotation, comes to bear against an end face 50 of the front end of the handle part 34. Upon a continuing screw-on motion of the brush part 32 or a corresponding screw-in motion of the handle part 34 into the brush part 32, the threaded coupling rod 36, according to the thread pitch, is pulled out of the front end of the handle part 34, counter to the action of the pretensioning device 42, until the stop cam 46 engages in the axial recess 48 at the front end of the handle part 34 and adopts its non-twistable work setting which is axially braced relative to the handle part 34. If the brush part 32 is intended to be exchanged for a different, new brush head, the brush part 32 needs only to be pulled by the length of the stop cam 46, counter to the force of the pretensioning device 42, axially away from the end face 50 at the front end of the handle part 34, in order to unscrew the handle part 34, in the opposite direction of rotation, from the thread 44.

From FIG. 1, it can further be seen that a conical centering, ring 58 is disposed, at an axial distance from the thread 44, at the front end of the coupling rod 36. In the region of the mouth of the coupling opening 38 in the brush part 32, there is provided a correspondingly shaped, smooth-walled segment 37 of the coupling opening 38 for receiving the centring ring 58. The diameters of the thread 44 and of the centring ring 58 of the coupling rod 36 are dimensioned larger than that of the stem 62 of the coupling rod 36, which stem is mounted displaceably in the handle part 34. Expediently, the thread 44 and the centring ring 58 exhibit the same diameter. The stem 62 is provided, according to FIG. 3, with two diametrically opposing, longitudinally extending guide beads 64, 66, which are guided axially displaceably into corresponding longitudinal grooves 68, 70 in the neck 41 and ensure that the coupling rod 36 cannot be twisted.

As further shown by FIG. 2, the sliding bearing 40 in the handle part 34 for the coupling rod 36 is limited by a transverse wall 72, which serves as a stop for an annular shoulder 74 on the inner end of the coupling rod 36. The transverse wall 72 is provided with an axial bore 76 exhibiting a diameter which is smaller relative to the stem 62 of the coupling rod 36. Through this bore 76 in the transverse wall 72, a cylindrical guide rod 80 extends from that end of the stem 62 of the coupling rod 36 forming the annular shoulder 74, there being fastened to the outer end of this guide rod 80, by means of a frontal, cylindrical projection 84, a locking block 82. The projection forms an annular shoulder, on which is supported one end of a helical compression spring 86, the other end of which bears against an annular shoulder forming the axial bore 76 in the transverse wall 72. It can thus be seen that the brush part 32 can be pulled by its stop can 46 out of the axial recess 48 in the front end of the handle neck 41, counter to the action of the pretensioning spring 86, and can afterwards be unscrewed, by a rotational motion, from the coupling end of the coupling rod 36.

The locking block 82 fastened to the rear end of the guide rod 80 is a component part of a securing device 88. The securing device 88 exhibits on its top side facing the front side of the toothbrush, i.e. the side of the toothbrush against which the thumb of the user bears when the toothbrush is in use, a locking lever 90 in the form of a two-sided lever. The locking lever 90 is mounted rotatably in a swivel axle 92, which is perpendicular to the central longitudinal plane of the handle part 34 and which lies in a spigot-shaped bracket 96 jutting up from the inner side of a rear wall 94 of the hollow handle part 34 (FIG. 4). Disposed helically around the bracket 96 is a pretensioning spring 98, which acts upon that side of a feeler arm 100 of the double-armed locking lever 90 facing the locking block 82 and acts upon the said locking lever with the aim of locking the locking lever 90 with the locking block 82. The feeler arm 100 extends from the swivel axle 92 to the rear end of the handle part 34, whilst a locking arm 102 of the locking lever 90, which locking arm has a locking boss 104 at the outer end, is directed towards the brush part 32. The locking arm 102 is herein configured tapered in the direction of its locking boss on the side 106 facing away from the locking boss, so that this rear-sided taper 106 of the locking arm 102 forms with the inner side 108 of the box-shaped wall 110 of the handle part 34 an acute angle opening in the direction of the brush part 32, whenever the locking lever 90 engages in a transversely running locking groove 112 in the locking block 82 and secures the brush part 32 against an axial pull-out motion from the neck 41 of the toothbrush. The acute-angled free space allows an unlatching motion of the locking arm 102 from the locking block 82, as is more accurately described below.

The feeler arm 100 is provided, on its longitudinal side facing away from the locking block 82, with an actuating plate 116 angled-off in the direction of the rear wall 94 of the handle part 34. The actuating plate 116 lies behind an elastically configured wall segment 120, which is configured in that wall of the handle part 34 of the toothbrush lying opposite the feeler arm 100. The elastic wall segment 120 enables the locking lever 90 to be actuated. As is shown in FIG. 5, when pressure is applied to the elastic wall segment 120, the elastic wall segment 120 comes to bear against the actuating plate 116 situated behind it and moves the said actuating plate inwards up to the locking block 82, whereupon the feeler arm 100 moves laterally past the locking block 82, as is more accurately described later. Consequently, the locking arm 102 of the locking lever 90 moves away from the locking block 82, so that the locking boss 104 is released from the locking groove 112 in the locking block 82. The axial motion of the coupling rod 36 connected to the locking block 82 is thus no longer blocked, thereby enabling the brush part 32 to be pulled axially away from the handle part 34 and unscrewed from the thread 44.

As is shown in particular in FIGS. 6 and 7, that side of the locking block 82 lying opposite the feeler arm 100 is configured essentially flat at the rear end of the said locking block and exhibits a lug 122, which forms on the locking block 82 a shoulder 124 which runs straight, in the longitudinal direction of the toothbrush, in a rearward direction parallel to the central longitudinal axis of the toothbrush or ascends gently in the form of a ramp. Towards the end, the locking block 82 thickens out such that the surface lying opposite the feeler arm 100 ascends gradually, in a region 126, towards the surface of the lug 122, so that the shoulder 124 thus disappears back to the end of the locking block 82.

The locking lever 90 is of lamellar configuration in the plane perpendicular to the swivel axle 92 and is placed onto the bracket 96 in such a way that a feeler pin 128 attached to the rear end of the feeler arm 100, in the locking state of the locking lever 90 (cf. FIG. 2), bears under pretensioning upon the lug 122 of the locking block 82. The pretensioning is achieved by virtue of the fact that, in this position, the feeler arm 100 is bent elastically out of the plane lying perpendicular to the swivel axle 92 (FIG. 7).

The shoulder 124 running parallel to the central longitudinal axis or ascending gently in the direction of the rear end of the toothbrush forms, together with the region 126 ascending perpendicular to the lamellar plane of the feeler arm 100, a control cam unit for the feeler pin 128.

If, as shown in FIG. 5, a pressure is applied to the elastic wall segment 120 and the feeler arm 100 is thereby moved inwards, the feeler pin 128 slides over the lug 122 and engages on the shoulder 124 (FIGS. 8, 9). Even after the elastic wall segment 120 has been set free, the locking lever 90 is thus fixed in the setting in which the locking block 82 is freed and can be moved axially (FIG. 10). The user, in order to unscrew the brush part, is not therefore reliant upon simultaneously pressing onto the elastic wall segment 120 and pulling the brush part 32 away from the handle part 34, but is able to perform these actuating steps successively.

Once the brush part 32 is pulled away from the handle part 34, the locking block 82, along with the coupling rod 36, also moves to the left in the representation of FIG. 10. The feeler pin 128 hereupon slides along the shoulder 124 forming a control cam, until it reaches the thickening region 126. In the region 126, the feeler pin 128, counter to the elastic action of the lamellar form of the locking lever 90, is forced back outwards away from the locking block 82 (FIG. 11) and thereby disengaged from the shoulder 124, so that the locking lever 90 moves, under the action of the pretensioning spring 98, into the setting shown in FIG. 12, which setting corresponds to the setting of the locking lever 90 in FIG. 2, except that the locking boss 104 now bears behind the locking groove 112 against the locking block 82, since the latter has, of course, been moved to some extent in the direction of the neck 41 in order to screw on a new brush part 32. Once, after the new brush part 32 has been screwed on, its stop cam 46 has moved back into the axial recess 48 and the locking block 82 has thus moved to the right in the representation of FIG. 12, the locking boss 104 also finally engages in the locking groove 112 of the locking block 82 and again reaches the original setting shown in FIG. 2, in which the coupling rod 36 is blocked.

In FIGS. 13 and 14, a second embodiment of a securing device 200 for the toothbrush 30 is shown. The neck 41 of the toothbrush consists, in this embodiment, of a flexible plastic which, at the front end of the handle part 34 facing the brush part 32, is attached to the said handle part. Into this neck 41 there is inserted a separate housing 210 for the coupling device. In the front segment of the housing 210, the axial sliding bearing 40 for the stem 62 of the coupling rod 36, including the longitudinal grooves for the guide beads 64, 66, is configured on the stem 62. The front part of the housing 210 is closed off by the transverse wall 72. After the transverse wall 72, the housing 210 merges integrally into a rear segment surrounding the guide rod 80.

The securing device 200 comprises, like the securing device 88 of the first embodiment, a two-sided locking lever 220, which is rotatable about a swivel axle 222 perpendicular to the central longitudinal axis of the toothbrush and exhibits a locking arm 224 and a feeler arm 226. The feeler arm 226 is provided at its end with an actuating plate 228, which lies behind an elastic wall segment 230 in the wall of the handle part 34. The swivel axle 222 is located close to the transverse wall 72 and is attached to the housing 210.

The locking arm 224 extends beyond the region of the transverse wall 72 forward into a notch in the neck region 41 of the toothbrush. A locking boss 234 at the outer end of the locking arm 224 engages, in the locking state, in a notch 236 in one of the guide beads 64, 66 on the stem 62 of the coupling rod 36, which coupling rod is thereby blocked in terms of its axial mobility. The locking lever 220 is held in the locking state by a pretensioning spring 238, for example, as shown in FIG. 13, a leaf spring.

The elastic wall segment 230 can be configured in one piece with the neck 41 of the handle part 34; it then extends up to a hole in the wall of the relatively rigid handle part 34 and fills up the hole.

When pressure is applied to the elastic wall segment 230 and thereby to the actuating plate 228, the locking boss 234 is disengaged from the notch 236 and the coupling rod 36 thereby freed, which coupling rod thus allows the stop cam 46 to be pulled out of the axial recess 48 and hence allows the brush part 32 to be unscrewed and replaced.

In FIGS. 15 and 16, a third embodiment of the securing device is shown, which is similar to the second embodiment. In this third embodiment, the guide rod 80 is provided however with an extension 240, which juts through a second transverse wall 242, forming the closure of the housing 210, rearwards into the hollow handle part 34. The extension 240 exhibits, in the region behind the second transverse wall 242, a circumferential, radial notch 244, which serves as a locking groove in which the locking boss 234 of the locking arm 224 engages. For this purpose, the swivel axle is attached in the proximity of the second transverse wall 242 to the housing 210 and the locking arm 224 extends beyond the region of the second transverse wall 242 rearwards into the cavity in the handle part 34. In this embodiment also, the locking lever 220 is moved by means of an elastic wall segment 230 in the wall of the handle part 34 and an actuating plate 228 on the feeler arm 226.

Figure 17:
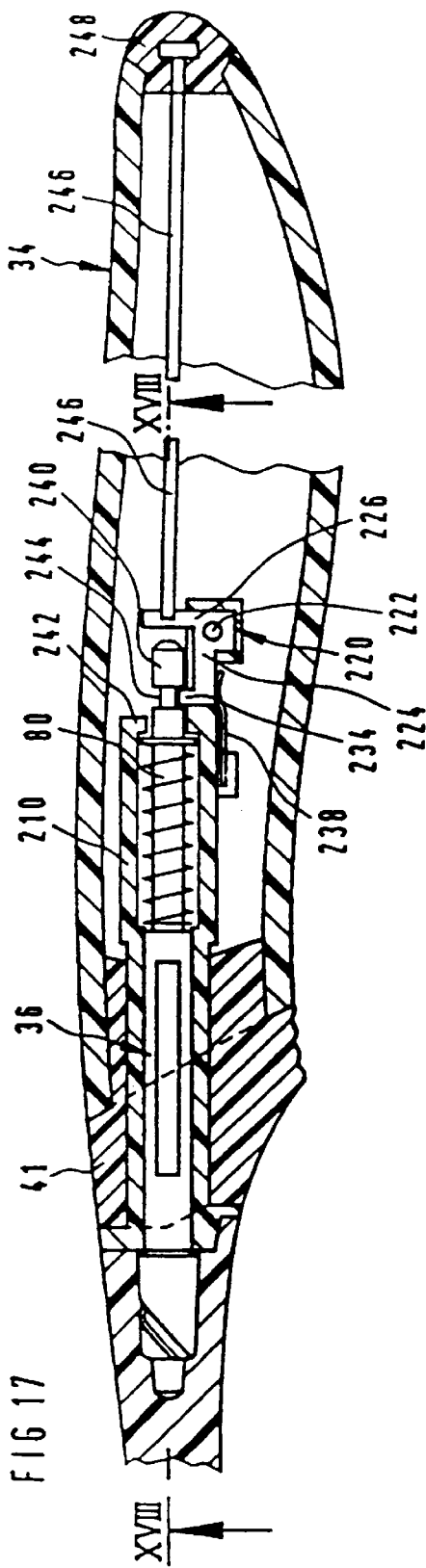
FIG. 17 shows a fourth embodiment of a toothbrush according to the invention exhibiting a securing device, essentially in a central longitudinal section.
Figure 18:
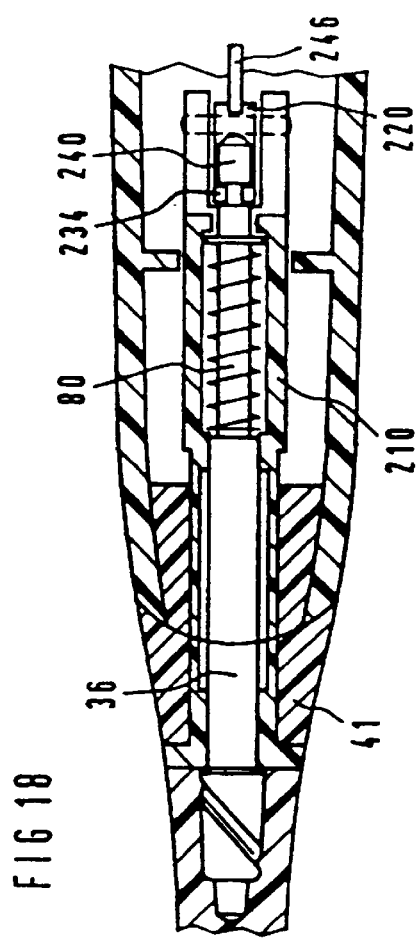
FIG. 18 shows a side view of the toothbrush in FIG. 17 according to the sectional line XVIII—XVIII.

In FIGS. 17 and 18, finally, a fourth embodiment of the securing device 200 is shown. In this securing device also, the guide rod 80 is provided with an extension 240, which extends rearwards through the second transverse wall 242. The locking arm 224 and the feeler arm 226 of the locking lever 220 are here however attached to each other at an angle of 90°, the swivel axle 222 still being situated behind the second transverse wall 242 and outside the central longitudinal axis of the toothbrush and the feeler arm 226 crossing this central longitudinal axis. An axial pressure at play in the central longitudinal axis thus enables the locking boss 234 of the locking lever 220 to be disengaged from the notch 244 in the extension 240. The axial pressure is applied to the feeler arm 226 by means of a pressure rod 246. The pressure rod 246 runs essentially along the central longitudinal axis of the handle part 34. The one end of the pressure rod 246 is fastened in an articulated manner to the feeler arm 226 and the other end thereof lies in an elastic endpiece 248 at the end of the handle part 34. When pressure is applied to the elastic endpiece 248, the pressure rod 246 moves to the left in the representation of FIG. 17, whereby the locking lever 220 is pivoted and the locking boss 234 frees the coupling rod 36.

REFERENCE SYMBOL LIST 30 toothbrush
32 brush part
33 bristle bed
34 handle part
36 coupling rod
37 smooth-walled segment
38 coupling opening
39 bristles
40 axial sliding bearing
41 neck
42 pretensioning device
44 thread
46 stop cam
48 axial recess
50 end face
58 centring ring
62 stem of 36
64,66 guide beads
68,70 longitudinal grooves
72 transverse wall
74 annular shoulder
76 bore of 72
80 guide rod
82 locking block
84 projection
86 spring
88 securing device
90 locking lever
92 swivel axle
94 rear wall
96 bracket
98 pretensioning spring
100 feeler arm
102 locking arm
104 locking boss
106 tapered side
108 inner side
110 wall of 34
112 locking groove
116 actuating plate
120 elastic wall segment
122 lug
124 shoulder
126 ascendant region
128 feeler pin
200 securing device
210 housing
220 locking lever
222 swivel axle
224 locking arm
226 feeler arm
228 actuating plate
230 elastic wall segment
234 locking boss
236 notch
238 pretensioning spring
240 extension of 80
242 second transverse wall
244 notch
246 pressure rod
248 elastic endpiece

We claim:

1. A toothbrush comprising;
an elongated brush part, which has a coupling end having a coupling opening;
an elongated hollow handle part, having a front coupling end and an axial bearing within the handle part, the hollow handle part having a wall;
a coupling device, having a coupling rod defining a longitudinal axis, said coupling rod exhibiting a first longitudinal segment, which is slidably mounted within the axial bearing of the handle part and which is removably connected to the brush part, and having a second longitudinal segment which extends from said first longitudinal segment to an outside of the axial bearing within the hollow handle part;
a return spring, which is disposed on the second longitudinal segment, the second longitudinal segment having two ends which are supported between bearings, so that the coupling rod is pretensioned in a direction opposite the brush part, said direction being parallel to the longitudinal axis of the coupling rod;
a latching device for rotationally locking the coupling end of the brush part and the coupling end of the handle part;
a securing device for preventing axial motion of the coupling rod, a first part of the securing device in contact with the coupling rod and a second part being movable between a securement setting and a release setting and being pretensioned by a spring towards the securement setting; and
an actuating device in the wall of the hollow handle part for actuating the second part of the securing device.

2. The toothbrush according to claim 1, characterized in that the first part of the securing device is a locking block, which extends essentially coaxially from the second longitudinal segment of the coupling rod and at a lateral distance from the wall of the handle part and which is provided with a locking groove.

3. The toothbrush according to claim 2, characterized in that the second, movable part of the securing device is a double-armed locking lever, which is mounted pivotably on a swivel axle in the handle part against the pretensioning force of the spring and whose one arm of the locking lever exhibits a locking boss which, in the securement setting, engages in the locking groove of the first part of the securing device, and whose other arm of the locking lever is actuated, by an elastic segment of the actuating device of the handle part, by the application of a pressure for freeing the securing device.

4. The toothbrush according to claim 3, characterized in that the elastic segment is disposed in a side portion of the wall of the handle part.

5. The toothbrush according to claim 3, characterized in that the double-armed locking lever is provided, at an end of said other arm of the locking lever facing away from the locking boss, with a feeler pin, an end of the locking block facing away from the brush part exhibits a shoulder and an ascending region, which form a control cam unit for the feeler pin.

6. The toothbrush according to claim 5, characterized in that the control cam unit exhibits a lug, which forms a bearing surface for the feeler pin in the securement setting.

7. The toothbrush according to claim 6, characterized in that the bearing surface is limited, when the locking lever moves from the securement setting towards the release setting, by the which is perpendicular to the bearing surface and which the feeler pin abuts in the release setting.

8. The toothbrush according to claim 1, characterized in that the first part of the securing device is a notch, serving as a locking groove, in the coupling rod.

9. The toothbrush according to claim 5, characterized in that the second, movable part of the securing device is a double-armed locking lever, which is mounted pivotably on a swivel axle in the handle part against the pretensioning force of the spring and whose one arm of the locking lever exhibits a locking boss which, in the securement setting, engages in the locking groove of the first part of the securing device, and whose other arm of the locking lever is actuated, by an elastic segment of the actuating device of the handle part, by the application of a pressure for freeing the securing device.

10. The toothbrush according to claim 9, characterized in that the swivel axle for the locking lever is attached to a housing, which is connected to the handle part and contains the axial bearing for the coupling rod.

11. The toothbrush according to claim 10, characterized in that the housing includes a wall which exhibits an aperture, the locking groove being disposed in the first longitudinal segment of the coupling rod in the region of the aperture.

12. The toothbrush according to claim 10, characterized in that at the rear end of the second longitudinal segment of the coupling rod there is located an extension, which juts out of a transverse wall closing off the housing, the extension being provided with the locking groove.

13. The toothbrush according to claim 9, characterized in that the actuating device contains an elastic endpiece at a rear end of the handle part facing away from the brush part, one end of a pressure rod held within the elastic endpiece, the other end of said pressure rod being connected to said other arm of the locking lever.

14. The toothbrush according to claim 9, characterized in that the elastic segment is disposed in a side portion of the wall of the handle part.

* * * * *